United States Patent [19]

Hussein

[11] 4,360,343
[45] Nov. 23, 1982

[54] METHOD FOR THE ORAL IMPLANTATION OF A DENTAL PROSTHESIS

[76] Inventor: Mamed Hussein, 408, rue Rougemont, Longueuil, Quebec, Canada, J4J 2B6

[21] Appl. No.: 204,077

[22] Filed: Nov. 4, 1980

[51] Int. Cl.³ .............................................. A61C 8/00
[52] U.S. Cl. .................................... 433/173; 433/176
[58] Field of Search ................................. 433/173-176

[56] References Cited

U.S. PATENT DOCUMENTS

| 3,683,501 | 8/1972 | Edelman | 433/176 |
| 3,738,008 | 6/1973 | Edelman | 433/176 |

*Primary Examiner*—Robert Peshock
*Attorney, Agent, or Firm*—Robic, Robic & Associates

[57] ABSTRACT

A method for the oral implantation of a dental prosthesis inside a tooth socket. This method comprises two basic steps, namely (a) creation of an artificial socket inside the maxillary bone and (b) implantation of a rigid support in the so-created socket to fix the prosthesis tooth. The first step is carried out by introducing a thin, sharp cutting tool having two cutting edges, in a predetermined direction in the depth of the bone using a thin probe as a guide for the blade, and subsequently opening the lateral walls of the hole formed by the cutting tool with a punch-shaped tool to create the artificial socket. The second step is carrying out by inserting inside the so created socket a scissors-like element comprising a pair of sharp blades each having a toothed edge, and subsequently separating these blades by introducing a thin pin between each other in such a manner that the teeth extending from the edges of the blades penetrate inside the walls or the artificial socket. To ease the introduction of the scissors-like element inside the socket, its blades can advantageously be located inside a toothed sleeve which can previously be inserted inside the artificial socket. The external ends of the pin and of the blades may serve as a support for the implantation of a prosthesis crown. This method advantageously allows the implantation of a dental prosthesis that is stable and rigid in position without loss of substance, risk of rejection and period of convalescence. These advantages result from the constriction of the blades between the walls of the artificial socket formed in the maxillary bone. An implant for use in the above described method is also disclosed and claimed.

12 Claims, 12 Drawing Figures

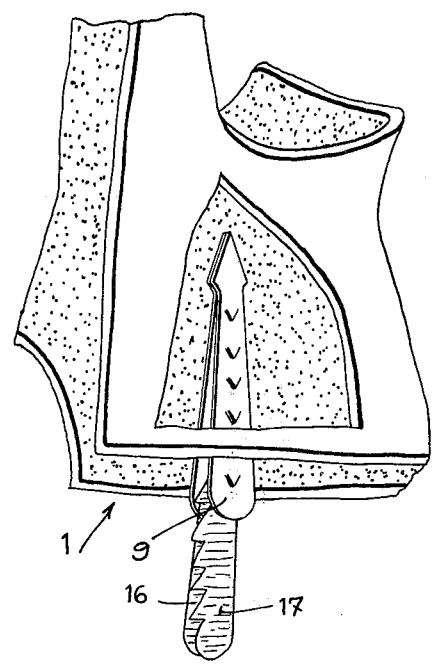
Fig. 11
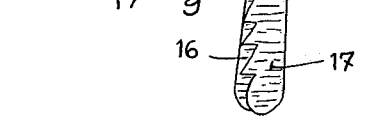
Fig. 11A
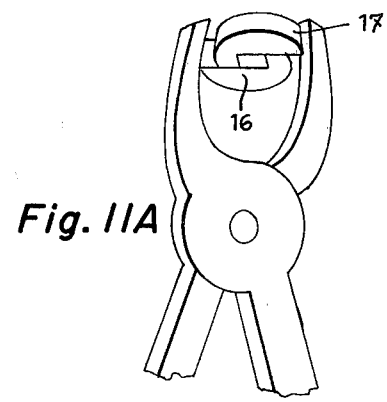
Fig. 12
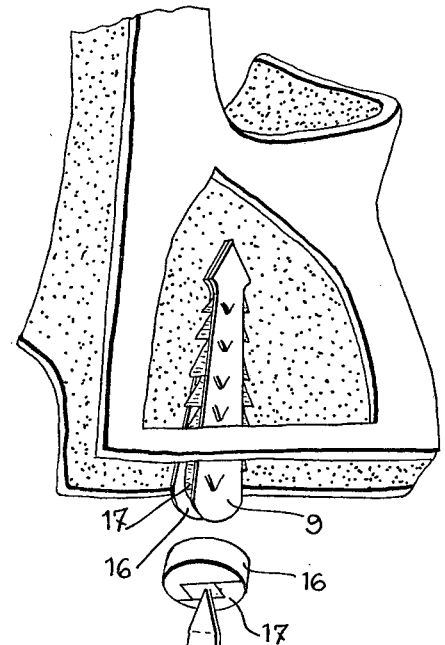
Fig. 12A
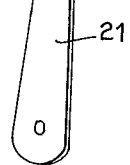

METHOD FOR THE ORAL IMPLANTATION OF A DENTAL PROSTHESIS

BACKGROUND OF THE INVENTION

The present invention relates to a method for the oral implantation of a dental prosthesis and to an implant for carrying out this method.

DESCRIPTION OF THE RELEVANT ART

As everybody knows, the main difficulties encountered by those skilled in the art of oral implantology, are directly associated to two basic problems that are, respectively, the problem of adhesion of the implant inside the maxillary bone and the problem of surgical rejection of the implant by the patient's body. Several solutions such as those disclosed in U.S. Pat. Nos. 2,745,180 and 3,797,111 have been proposed for simultaneously solving these two problems. However, none of these solutions has up to now proved to be satisfactory as, in every case, the adhesion is obtained only by lateral reinforcement of the mucuous membrane inside the natural socket, which reinforcement is in practice either completely absent or insignificant when taking into account the pressure and stress that the implant must support when the patient is, for example, chewing or eating.

Actually, the present inventor who is a dental surgeon, has found that, up to now, the implant was planted inside the natural socket as seeds are planted in the earth, hoping that the seeds will grow and give some roots that in turn, will give to the plants their rigidity, instead of installing the implant as a solid building is constructed on the ground. As the result of this discovery, the present inventor has understood that instead of surgically "ploughing" the maxillary bone as is presently done for installing an implant, it should be better to expand a rigid structure inside the bony substance of the body, which substance is characterized by its lack of rigidity and its spongious density, in order to both conserve the bony substance as such and to give a rigid base to the implant.

The advantage of proceeding of such an expansion of an implant inside the maxillary bone resides not only in that it gives a good rigidity and tenacity to the implant but also in that it avoids formation of cavities or "vacuum" that may enclose air and lead after some period of time to the rejection phenomenae that everybody knows.

SUMMARY OF THE INVENTION

The present invention thus proposes a method for the oral implantation of an implant inside a tooth socket, which comprises two basic steps, namely, the creation of an artificial socket inside the maxillary bone and the implantation of an implant inside this artificial socket. Both of these steps are carried out by expansion of an implant inside the bony substance, without loss of substance, risk of rejection and period of convalescence.

The first step of the method according to the invention is carried out by moving a thin, sharp cutting tool provided with two cutting edges, in a predetermined direction in the depth of the bone using a thin probe as a guide for the cutting blade, and, subsequently, opening the lateral walls of the artificial socket previously formed by the cutting tool with a punch-shaped tool having surfaces thereon suitable for expanding the lateral walls so as to enlarge the same.

The second step of the method according to the invention is carried out by inserting a scissors-like element. prosthesis or implant comprising a pair of sharp blades or elongated parts each having a tooth or serrated edge inside the so-created socket, and subsequently separating the so-inserted blades by introducing a thin pin or separating member between them in such a manner that the teeth extending from the edges of the blades penetrate inside the walls of the artificial socket because of their lateral expansion. More particularly, the method for the oral implantation of a dental implant inside of a tooth socket according to the invention is characterized in that it comprises the steps of:

(a) forming an artificial socket inside the maxillary bone with a thin, sharp cutting tool provided with two cutting edges;

(b) opening the lateral walls of the so formed artificial socket with a first element which is a punch-shaped tool having surfaces thereon suitable for expanding the lateral walls;

(c) inserting a scissors-like second element or implant inside the opened socket, this element comprising a pair of sharp blades each having a serrated edge on an outer surface of each part, each blade also comprising an outer surface and a beveled recess extending centrally along an inner surface thereof for substantially all of its length, these blades being kept together during their insertion inside the socket by engaging the beveled recess of one blade into the beveled recess of the other blade in such a manner that the teeth of each blade be hidden by the outer surface of the other corresponding blade;

(d) introducing a thin separating member or pin having two beveled edges between the beveled recesses of the blades so as to laterally separate the same and thus to ensure penetration of the teeth of each blade up to now hidden by the other blade into the walls of the artificial socket; and (e) fixing a prosthesis crown directly to the external ends of the pin and sharp blades of the scissors-like element.

This method allows the implantation of prosthesis that are stable and rigid in position without requiring any period of convalescence, simply because of the horizontal expansion of the blades of the scissors-like element inside the walls of the artificial socket formed in the maxillary bone.

In accordance with a preferred embodiment of the invention, a third element or sleeve can be additionally inserted inside the socket before inserting the scissors-like element. The sleeve comprises two symetrical tongues or portions each having an elongated trapezoidal shape, which are connected to each other at their upper ends by a small expansion or cap having a triangular shape. The cap which forms an integral part of the sleeve is hard and sharp and has cutting edges. These tongues each comprise a plurality of punched-out teeth projections on their external surfaces. The sleeve is inserted inside the artificial socket before the insertion of the scissors-like element in order to increase the thickness of the implant when the same is inserted inside the socket and thus to ensure horizontal expansion of the same in four perpendicular directions instead of two directions only as is obtained when use is made of the scissors-like element only.

In order to reduce into practice the above described method, the present invention also proposes an implant especially designed for being inserted in an artificial tooth socket.

In accordance with the present invention, this implant comprises:

(a) a scissors-like element or implant comprising a pair of sharp blades or elongated parts each having a toothed or serrated edge, each blade also comprising a bevelled recess extending centrally along substantially all its length, these blades being kept together during their insertion inside the socket by engaging the bevelled recess of one blade into the bevelled recess of the other blade in such a manner that the teeth of each blade be hidden by the surface of the other corresponding blade; and (b) a thin pin or separating member having two bevelled edges, this thin pin being designed to be introduced between the bevelled recesses of the blades to laterally separate the same and thus to ensure penetration of the teeth of each blade hidden by the other blade inside the walls of the artificial socket.

In accordance with a preferred embodiment of the invention, the implant can further comprise a sleeve having two symetrical tongues or elongated portions each having an elongated trapezoidal shape. The tongues are connected to each other at their upper ends by a small cap or expansion having a triangular shape. This cap which forms an integral part of the sleeve is hard and sharp and has cutting edges. The tongues each comprises a plurality of punched-out teeth or projections on their external surfaces. This sleeve is designed to be inserted in the artificial socket before the insertion of the scissors-like element in order to increase the thickness of the implant when the same is inserted inside the socket and thus to ensure horizontal expansion of the same in four perpendicular directions instead of two directions only as is obtained when use is made of the scissors-like element only.

BRIEF DESCRIPTION OF THE DRAWING

The invention and its advantages will be better understood with reference to the following description of an embodiment thereof taken in correction with the accompanying drawings in which:

FIGS. 11, 11a, 12 and 12a show the insertion of the scissors-like element into the sleeve inside the opened socket; and FIG. 13 shows the insertion of the pin between the blades of the element.

DETAILED DESCRIPTION OF THE PREFERRED EMBODIMENT

Figure 1:
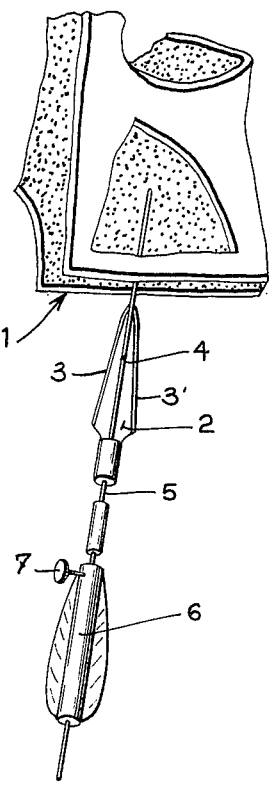
FIGS. 1 and 2 show the formation of an artificial tooth socket inside a maxillary bone with a thin, short cutting tool having two cutting edges.
Figure 2:
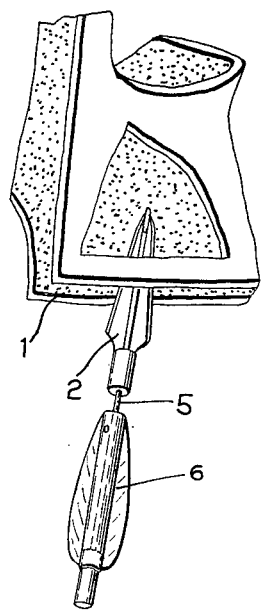
Figure 3:
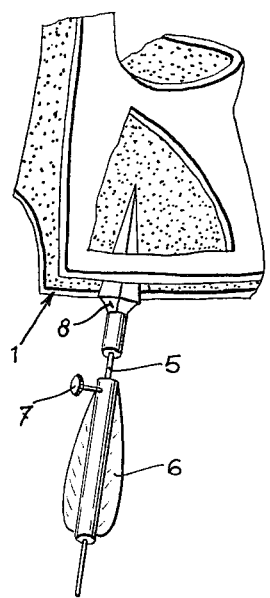
FIG. 3 shows the opening of the lateral walls of the so-formed artificial socket with an enlarging punch-shaped tool.

The method for the oral implantation of a dental prosthesis according to the invention is carried out in two steps. The first step essentially consists in forming an artificial tooth socket inside the maxillary bone 1, as is shown on FIGS. 1 and 2. To form this socket, use is made of a thin, sharp cutting tool 2 provided with two cutting edges 3 and with a longitudinal guiding hole 4. The hole 4 is designed to receive a guiding probe comprising a rigid, linear stem 5 and a handle 6 detachably fixed onto the stem by a fixation screw 7. The stem 5 is exclusively used for guiding the cutting tool 2 in a predetermined direction so that this tool may be used for forming an artificial socket at desired location and depth in the maxillary bone 1.

In operation, after having fixed the handle 6 to the stem 5 by its fixation screw 7, the probe is inserted in the spongious part of the bone between the lateral arches of the maxillary bone, at a depth of about 18 mm that can be marked onto the stem for the purpose of simplification. The screw 7 is then unscrewed to release the handle 6 which then may slide on the stem 5 behind the cutting tool 2. As soon as unscrewed, handle 6 is used to push the cutting tool 2 into the bone 1 in the predetermined direction defined by the stem 5. If necessary, use can be made of a hammer or of a similar tool for driving in the tool 2 pushed by the handle 6. Once the cutting tool is inserted at the desired depth in the maxillary bone 1, the stem 5 is first removed by its handle and the cutting tool 2 is subsequently pulled out with tongs.

The first step of the method according to the invention has to be completed by opening the lateral walls of the preformed artificial socket. To do so, use is made of an enlarging punch-shaped tool 8 that can be fixed directly to the stem 5 or to another stem. The punch 8 can also be driven in the maxillary bone using the handle 6. After it has been driven in, the punch-shaped tool 8 is pulled out with tongs. This insertion of the punch 8 in the bone results in the creation of an opened artificial socket A without loss of bony substance.

Figure 4:
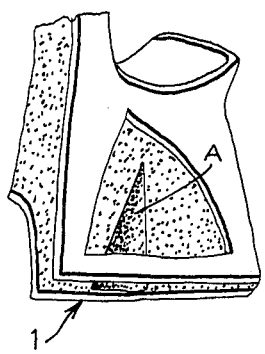
FIG. 4 shows the general shape of the artificial socket after it has been opened.

As can be seen on FIG. 4, the artificial socket A which is so formed, has an oval-shaped opening. Indeed, only the spongious part of the bone already weakened by the presence of the natural socket are horizontally expanded by the punch-shaped tool during its insertion, the external and posterior arches of the bone being then slightly opened only or not at all owing to their natural rigidity. The formation and use of a socket having such an oval shaped opening is completely different from what has been done and used up to now, as use was systematically made up to now of sockets with openings having a cylindrical or conical shape and involving complete destruction or deformation of both arches of the bone and, as a consequence, substantial reduction in rigidity and therefore adherence. Actually, it appears that all the dental prosthesis that have been made and used up to now are of a cylindrical or conical shape because they are especially designed to be inserted in natural tooth sockets. Even if this kind of already known prosthesis was inserted into an oval shaped artificial socket as disclosed hereinabove, there would not be perfect adhesion and complete elimination of the rejection phenomenae as the prosthesis would not be perfectly maintained in all directions especially because of the oval shape of the opening.

A sleeve 9 can be inserted into the artificial socket 5 after it has been opened by the punch shaped tool 2. The sleeve 9 comprises two symmetrical tongues 10 and 11 each having an elongated trapezoidal shape. These tongues are connected to each other at their upper ends by a small cap 13 having a triangular shape. The cap 13 which forms an integral part of the sleeve, is hard and sharp and has two cutting edges. The external surfaces of the tongues 10 and 11 that can be made of gold or chromium, are provided with a plurality of small, punched out teeth 14 designed to engage the internal walls of the socket. The use of this sleeve is not always necessary. As a matter of fact, this sleeve must only be used when it is required to increase the thickness of the implant and thus to ensure horizontal expansion of the same in four perpendicular directions instead of two directions only. As can be understood, the engagement of the teeth 14 inside the bone, improves the adherence of the implant inside the socket.

Figure 6:
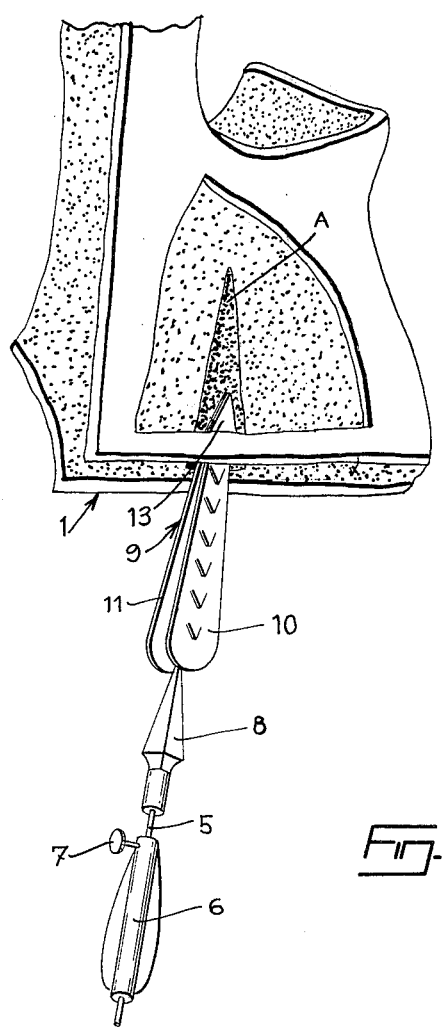
FIG. 6 shows the insertion of the sleeve inside the opened socket.
Figure 5:
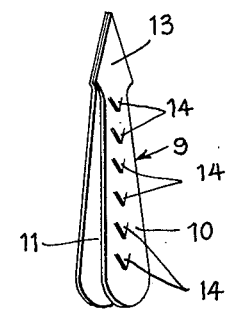
FIG. 5 is a perspective view of a sleeve used for increasing the thickness of the implant.
Figure 7A:
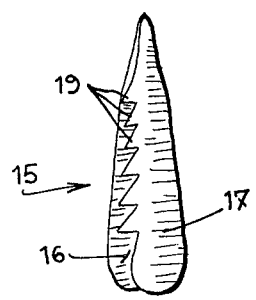
FIGS. 7a and 7b are side and bottom views of the scissors-like element to be inserted in the opened socket, with the blades of the implant kept together.
Figure 8A:
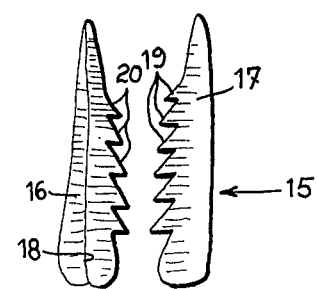
FIGS. 8a and 8b are views similar to those of FIGS. 7a and 7b except that the blades are separated.
Figure 7B:
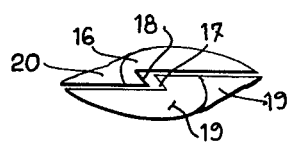
Figure 8B:
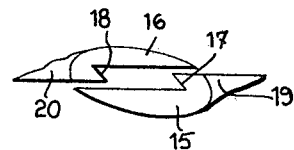

The insertion of the sleeve 9 inside the socket can be made, using the punch-shaped tool 8 as is shown on FIG. 6. When the sleeve is inserted, then the implant can be inserted inside the socket A. The implant which is illustrated in detail on FIGS. 7 and 8 is constituted by a scissors-shaped element 15 made of, for example, vitalium. The element 15 comprises a pair of sharp blades 16 and 17 that are identical in shape and are especially designed to longitudinally match one against the other to form a compact insert having a general, oval shaped cross-section as shown on FIG. 7b. The oval cross-section of the insert substantially facilitate its insertion into the socket A.

In order to form together an insert having an oval shaped cross-section, each blade 16 or 17 comprises a beveled recess 17a or 18 extending centrally along substantially all of its length. Each blade 16 or 17 also comprises a set of teeth 19 or 20 that are sized in such a manner that they may be completely "hidden" by the flat surface of the opposite blade when the blades 16 and 17 are kept together with the groove 17a inserted into the groove 18 as shown on FIG. 7b. This particular structure advantageously permits each blade to hide the teeth of the other blade while simultaneously reducing the general volume of the insert during its insertion inside the opened socket A as is shown on FIG. 11. This "withdrawal" of the teeth of the blades of course substantially facilitates the insertion of the scissors-like element into the socket while simultaneously avoiding scratching of the bone.

Figure 9:
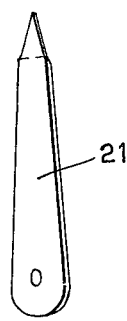
FIG. 9 is a side elevational view of the pin used for separating the blades of the implant.
Figure 10:
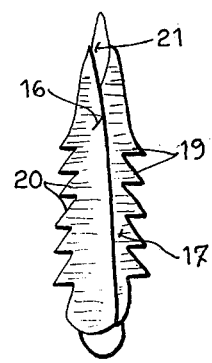
FIG. 10 shows a general aspect of the implant when the pin has been inserted.

When the element 15 has been inserted in the socket A, its blades 16 and 17 are opened inside the tongues 10 and 11 of the sleeve 9 to ensure penetration of the teeth 19 and 20 into the bone in two opposite horizontal directions. To ensure this separation of the blades ensuring a complete penetration of their teeth and of the teeth of the sleeve 9 inside the walls of the artificial socket, use is made of a thin pin 21 which has two bevelled edges. The pin 21 is inserted between the recesses 17a and 18 of the blades 16 and 17 as is shown in FIGS. 9, 10 and 12. To facilitate the insertion of the pin, one can press the external ends of the blades 16 and 17 as shown in FIG. 11a with tongs. Indeed, such a pressure exerted by the tongs, slightly separates the blades from each other while simultaneously initiating the penetration of their teeth inside the walls of the socket. Once this operation has been completed, the pin 21 can then be easily inserted into the opened space created between the recesses of the blades. The insertion of the pin which is shown in detail on FIG. 12 and 12a, of course fully completes the expansion of the implant in the socket while keeping the blades of the implant fully separated in a very stable manner as shown in FIG. 13.

After having completed the latter step, a prosthesis crown can finally be fixed in a conventional manner directly onto the external ends of the pin 21 and blades 16 and 17.

The above described method in which an implant is rigidly fixed in a very strong manner directly inside the bone without formation of cavities or "vacuum", advantageously permits to implant a very stable and rigid prosthesis without risk of rejection or period of convalescence.

In this regard, it should be noted that the present inventor has already tested his method on several patients. These patients just after their surgical operations, were able to eat and bite an apple or another fruit of the same nature without pain and even sign that the prosthesis was tearing out.

The embodiments of the invention in which an exclusive property or privilege is claimed are defined as follows:

1. An implant to be inserted into an artificial tooth socket, said implant comprising:
   (a) a pair of elongated parts each having an inside surface and an outside surface;
   (b) each of said parts having a complementary beveled recess on said inside surfaces;
   (c) serrated edges positioned on an outer surface of each part;
   (d) said beveled recesses being interengaged upon insertion whereby said serrated edges on each part do not extend beyond the outer surface of the other part during insertion; and
   (e) a separating member having beveled edges engaging said beveled recesses in said elongated parts whereby said separating member when inserted into said beveled recesses of said elongated parts comprising said implant separates said first elongated part from said second elongated part and drives said serrated edges of said elongated parts into the walls of the artificial socket.

2. An implant according to claim 1 further comprising a sleeve having two symmetrical portions each having an elongated shape, said portions being connected to each other at one end thereof by a substantially triangularly shaped expansion, said expansion forming an integral part of said sleeve, said expansion being hard, sharp and having cutting edges, said portions having external surfaces and a plurality of projections thereon whereby said sleeve increases the thickness of said implant and fixes said implant in at least four directions.

3. An implant according to claim 1, wherein said implant is made of vitallium.

4. An implant according to claim 2, wherein said sleeve is made of gold.

5. An implant according to claim 2, wherein said sleeve is made of chromium.

6. An implant according to claim 1, wherein said beveled recess on said inside surface extends substantially the length thereof.

7. An implant according to claim 1, wherein said separating member is tapered at one end thereof.

8. An implant according to claim 1 wherein said separating member is tapered along substantially the entire length thereof.

9. A method for the oral inplantation of an implant inside a tooth socket, said method comprising the steps of:
   (a) forming an artificial socket in the maxillary bone of a patient with a thin, sharp cutting blade provided with two cutting edges;
   (b) opening the lateral walls of the so-formed artificial socket with a first element having surfaces thereon suitable for expanding said lateral walls;
   (c) inserting an implant inside said open socket, said implant comprising:
      (i) a pair of elongated parts each having an inside surface and an outside surface,,
      (ii) each of said parts having a complimentary beveled recess on said inside surfaces,
      (iii) serrated edges positioned on an outer surface of each part,
      (iv) said beveled recesses being interengaged upon insertion whereby said serrated edges on each part do not extend beyond the outer surface of the other part during insertion;
   (d) introducing a separating member having beveled edges formed to engage said complimentary beveled recesses in said elongated parts and separating said elongated parts by inserting said separating member into said recesses whereby said serrated edges of said elongated parts are driven into the walls of said artificial socket formed in said maxillary bone; and
   (e) fixing a dental prosthesis directly to the external end of said separating member and said implant.

10. The method as defined in claim 9, comprising the additional step of inserting a sleeve inside said artificial socket before inserting said implant and after expanding said socket, said sleeve comprising two symmetrical portions each having an elongated shape, said portions being connected to each other at one end thereof by a triangularly shaped expansion, said expansion forming an integral part of said sleeve, said expansion being hard, sharp and having cutting edges, said portions having external surfaces and a plurality of projections thereon, whereby said sleeve increases the thickness of said implant and fixes said implant in at least four directions.

11. The method as defined in claim 9 or 10, wherein said forming step is accomplished by incising said maxillary bone.

12. The method as defined in claim 9 or 10, wherein said opening step is accomplished by compressing said lateral walls with said first element.

* * * * *